(12) United States Patent
Broderick et al.

(10) Patent No.: US 11,097,099 B2
(45) Date of Patent: Aug. 24, 2021

(54) MULTIPLE TISSUE LAYER ELECTROPORATION APPLICATOR AND DEVICE

(75) Inventors: Kate Broderick, San Diego, CA (US); Feng Lin, San Diego, CA (US); Jay McCoy, San Diego, CA (US); Stephen V Kemmerrer, San Diego, CA (US); Rune Kjeken, Oslo (NO)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 1795 days.

(21) Appl. No.: 13/581,700

(22) PCT Filed: Mar. 1, 2011

(86) PCT No.: PCT/US2011/026688
§ 371 (c)(1),
(2), (4) Date: Aug. 29, 2012

(87) PCT Pub. No.: WO2011/109399
PCT Pub. Date: Sep. 9, 2011

(65) Prior Publication Data
US 2012/0323165 A1    Dec. 20, 2012

Related U.S. Application Data

(60) Provisional application No. 61/309,423, filed on Mar. 1, 2010, provisional application No. 61/309,860, filed on Mar. 2, 2010.

(51) Int. Cl.
*A61N 1/32* (2006.01)

(52) U.S. Cl.
CPC .................................. *A61N 1/327* (2013.01)

(58) Field of Classification Search
CPC .. A61N 1/0452; A61N 1/0476; A61N 1/0502; A61N 1/0504; A61N 1/306; A61N 1/327; A61M 5/3295; A61M 5/3298; A61M 5/46
See application file for complete search history.

(56) References Cited

U.S. PATENT DOCUMENTS

| | | | |
|---|---|---|---|
| 6,516,223 B2 | 2/2003 | Hofmann et al. | |
| 6,697,669 B2 | 2/2004 | Dev et al. | |
| 7,922,709 B2 | 4/2011 | Zhang et al. | |
| 2006/0084938 A1* | 4/2006 | Zhang | A61N 1/327 604/501 |
| 2007/0156082 A1 | 7/2007 | Scherman et al. | |
| 2008/0091135 A1* | 4/2008 | Draghia-Akli | A61N 1/327 604/20 |
| 2010/0323001 A1* | 12/2010 | Pachuk | C12N 15/111 424/450 |

\* cited by examiner

*Primary Examiner* — Bhisma Mehta
*Assistant Examiner* — Larry R. Wilson
(74) *Attorney, Agent, or Firm* — BakerHostetler

(57) ABSTRACT

The present invention relates to dual depth electroporation devices capable of electorporating both muscle tissue and skin tissue in a single application in order to generate a broad immune response in a subject, and uses of the same.

21 Claims, 5 Drawing Sheets

ID: 4X4, 15V, 3x100 ms
IM: 4P, 100V, 2x60 ms
ID/IM(Separate): 4x4(ID), 4P(IM), 1cm apart
Dual-depth (ID/IM together): One site (skin and underneath skeleton muscle)

MULTIPLE TISSUE LAYER ELECTROPORATION APPLICATOR AND DEVICE

CROSS-REFERENCE TO RELATED APPLICATIONS SECTION

This application is a 371 National stage entry of International Application No. PCT/US2011/026688, filed Mar. 1, 2011, and claims the benefit of U.S. Provisional Application Nos. 61/309,423, filed Mar. 1, 2010 and 61/309,680, filed Mar. 2, 2010, the contents of which are incorporated herein by reference.

BACKGROUND

Electroporation technology is currently being researched in conjunction with DNA vaccines, and other biologicals, to enhance delivery into cells of mammals in vivo. While this technology is known, there have been limitations to it that have prevented successful advancement of electroporation assisted DNA vaccine products. And, as a result, there are been various attempts and modifying or enhancing electroporation technology, whether it relates to the hardware, software, electrical pulse parameter, site of application (on subject), electrode sizes, or electrode array arrangement, among others.

Historically, EP has been performed in muscle tissue to achieve transfection (Intramuscular or IM) with DNA plasmids, resulting in the transfected muscle cells to synthesize and present antigenic proteins resulting in the generation of an immune response. In the case of a DNA vaccine, vaccination is employed to produce either therapeutic or prophylactic protection.

EP of the skin (Intradermal or ID) has been studied due to the accessibility of the tissue and its immunocompetency which may offer a different immune response profile than muscle EP. Still, there has been a lack of positive data shown protective immune response from DNA vaccination to skin tissue along with EP. Researchers recognize the potential benefits from each: muscle tissue as a target for EP achieves robust cellular responses and longer expression kinetics; skin tissue as a target for EP generates robust antibody titers.

Thus, there still remains a need for the improvement of in vivo electroporation techniques, especially in conjunction with DNA vaccine delivery. More particularly, there is a need for an electrode assemble that can better assist transfection of cells to elicit good immune responses.

SUMMARY OF INVENTION

In one aspect of the invention, there are dual depth electroporation devices capable of electorporating both muscle tissue and skin tissue in a single application, comprising: a electrical pulse generator; an array in electrical communication with said electrical pulse generator, said array having a first set of needle electrodes and a second set of electrodes. The first set of needle electrodes is for intramuscular delivery of a first electrical pulse and the second set of electrodes is for intradermal delivery of a second electrical pulse. The first set of needle electrodes have a length of about 10 mm to about 35 mm; whereas, the second set of needle electrodes having a length of about 0.01 mm to about 4 mm.

In another aspect of the invention, there are methods of generating a broad immune response in a subject by administering a biomolecule to both muscle tissue and skin tissue by electroporation assisted delivery using the dual depth electroporation devices described herein. The methods include injecting a biomolecule to both muscle and skin tissue; inserting the array, comprising inserting the first set of needle electrodes into muscle tissue and inserting the second set of needle electrodes into skin tissue. The first set of needle electrodes deliver the first electrical pulse to the muscle tissue; while the second set of needle electrodes deliver the second electrical pulse to the skin tissue to permit transfection of the biomolecule. This allows the subject's immune system to generate broad immune response including humoral and cellular response to the injected biomolecule.

BRIEF DESCRIPTION OF THE DRAWINGS

The numerous objects and advantages of the present invention may be better understood by those skilled in the art by reference to the accompanying figures, in which.

DETAILED DESCRIPTION OF PREFERRED EMBODIMENTS

Figure 1:
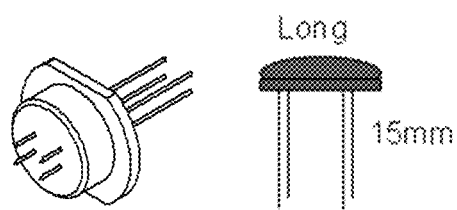
FIG. 1 displays an equal 15 mm length muscle electrode array.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller. The current amperage values described to be delivered by the devices herein are preferably constant current amperage values.

The term "constant voltage" is used herein to define a voltage or electric potential that is received or experienced by a tissue, or cells defining said tissue, over the duration of an electrical pulse delivered to same tissue. The electrical pulse is delivered from the electroporation devices described herein. This voltage remains at a constant voltage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output so the voltage in same tissue remains constant throughout the electrical pulse (on the order of microseconds), and from pulse to pulse. In some embodiments, the feedback element comprises a controller. The voltage values described to be delivered by the devices herein are preferably constant voltage values.

The term "feedback" or "current feedback" is used interchangeably and means the active response of the provided skin EP devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the skin EP device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The term "biomolecule" as used herein refers to nucleic acid sequences, proteins, lipids, microbubbles (e.g. drug-loaded vesicles), and pharmaceuticals.

The terms "electroporation," "electro-permeabilization," or "electro-kinetic enhancement" ("EP") as used interchangeably herein refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "minimally invasive" as used herein refers to a limited penetration by the needle electrodes of the provided electroporation device, and can include noninvasive electrodes (or nonpenetrating needles). Preferably, the penetration is to a degree that penetrates through stratum corneum, and preferably enters into outer most living tissue layer, the stratum granulosum, but does not penetrate the basal layer. Penetration depth not to exceed 0.1 mm, and preferably depth of at least 10-40 μm to break through stratum corneum. Preferably, this is accomplished using an electrode that has a trocar end ground to provide a sharp point that allows penetration through the stratum corneum but avoid deep penetration.

The term "tolerable" or "painless," is used herein interchangeably, and when referring to electroporation, means a substantially lower level of pain associated with electroporation than typical with available electroporation devices. More specifically, the tolerable (or painless) electroporation is the result of combination of using the minimally invasive electrodes described herein along with low electrical fields, preferable low voltage levels, i.e., from about 0.01V to about 70 V, about 1V to about 50 V, about 1V to about 20 V, about 1V to about 15 V, and preferably about 15 V.

An aspect of the present invention, referred to herein from time to time as a dual depth device, combines two different electroporation (EP) routes into one device to achieve a more balanced immune response and greater than either of the individual methods or the sum of the individual methods together. The device consists of combined electrode arrays from both the IM and ID methods. There are three methods to be combined: muscle, invasive dermal and minimally invasive (surface) dermal. The three combinations are: muscle with invasive dermal, muscle with minimally invasive (surface) dermal and invasive dermal with minimally invasive (surface) dermal.

In one aspect of the invention, there are dual depth electroporation devices capable of electorporating both muscle tissue and skin tissue in a single application, comprising: a electrical pulse generator; an array in electrical communication with said electrical pulse generator, said array having a first set of needle electrodes and a second set of electrodes. The first set of needle electrodes is for intramuscular delivery of a first electrical pulse and the second set of electrodes is for intradermal delivery of a second electrical pulse. The first set of needle electrodes have a length of about 10 mm to about 35 mm; whereas, the second set of needle electrodes having a length of about 0.01 mm to about 4 mm.

In some embodiments, the devices have the first set of needle electrodes deliver the first electrical pulse to muscle tissue and the second set of needle electrodes deliver the second electrical pulse to skin tissue, and preferably with nominal overlap. The electrical pulse generator can deliver through the first set of needle electrodes the first electric pulse of from 1 volt to about 200 volts and through the second set of needle electrodes the second electric pulse of from 1 volt to about 200 volts for the invasive dermal electrodes, preferably 100 volts, or from 1 volt to about 50 volts for the minimally invasive dermal electrodes, preferably 15 volts. This delivery can be simultaneous or separate, and if separate, can occur in any sequential order, preferably, the first electric pulse occurs first and the second electric pulse occurs after the first electric pulse. Each of the first electric pulse and the second electric pulse, individually, can be repeated up to 6, 5, 4, 3, or 2 times. Preferably, the first pulse is repeated two times and the second electric pulse is repeated three times. The first electric pulse can deliver a current ranging from about 50 mA to about 500 mA, and the second electric pulse can deliver a current ranging from about 50 mA to about 500 mA for the invasive dermal electrodes, preferably about 100 mA, or from about 1 mA to about 50 mA for the minimally invasive dermal electrodes, preferably about 10 mA. Each of the first electric pulse and the second electric pulse, individually, has a duration from 5 msec to about 250 msec, preferably 60 msec for the first electric pulse and 100 msec for the second electric pulse.

In some embodiments, the second set of electrodes can have a generally blunt distal end (end that is inserted into subject) with a sharp tip (or sharp central point) that allows penetration through the stratum corneum into the underlying epidermal tissue above the basal layer, preferably penetration through the stratum corneum is limited and enough to enter the distal end into the subsequent layer of the epidermis.

In another aspect of the invention, there are methods of generating a broad immune response in a subject by administering a biomolecule to both muscle tissue and skin tissue by electroporation assisted delivery using the dual depth electroporation devices described herein. The methods include injecting a biomolecule to both muscle and skin tissue; inserting the array, comprising inserting the first set of needle electrodes into muscle tissue and inserting the second set of needle electrodes into skin tissue. The first set of needle electrodes deliver the first electrical pulse to the muscle tissue; while the second set of needle electrodes deliver the second electrical pulse to the skin tissue to permit transfection of the biomolecule. This allows the subject's immune system to generate broad immune response including humoral and cellular response to the injected biomolecule.

In some embodiments, the disclosed methods include the injecting step occurring prior to the inserting step. The delivering step can comprise delivering through the first set of needle electrodes the first electric pulse of from 1 volt to about 200 volts and through the second set of needle electrodes the second electric pulse of from 1 volt to about 200 volts for the invasive dermal electrodes, preferably 100 volts, or from 1 volt to about 50 volts for the minimally invasive dermal electrodes, preferably 15 volts. The delivering step can include repeating each of the delivering first electric pulse and delivering the second electric pulse, individually, up to 6, 5, 4, 3 or 2 times. Preferably, the first pulse is repeated two times and the second electric pulse is repeated three times. The delivering step can include simultaneous or separate delivering of first electric pulse and second electric pulse, and if separate, can occur in any sequential order. Preferably, the delivering of the first electric pulse occurs first and the delivering of the second electric pulse occurs after the first electric pulse. The methods also include the delivering step having the first electric pulse delivering a current of from about 50 mA to about 500 mA, and the second electric pulse delivering a current ranging from about 50 mA to about 500 mA for the invasive dermal electrodes, preferably about 100 mA, or from about 1 mA to about 50 mA for the minimally invasive dermal electrodes, preferably about 10 mA. Each of the first electric pulse and the second electric pulse, individually, has a duration from 5 msec to about 250 msec, preferably 60 msec for the first electric pulse and 100 msec for the second electric pulse.

Figure 2:
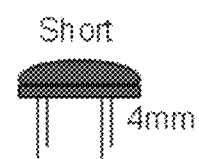
FIG. 2 displays an equal 4 mm length muscle electrode array.
Figure 3:
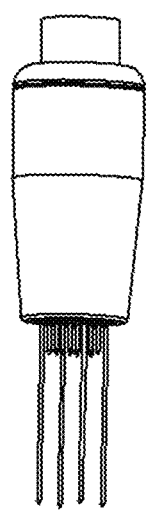
FIG. 3 displays one embodiment of the present invention: a 4×4 electrode array wherein the IM electrode are the corners of 4×4 array, while the remaining 12 electrodes can be either 3 mm invasive dermal or the pointy surface dermal style.
Figure 4:
FIG. 4 displays one embodiment of the present invention: a 4×4 electrode array wherein the corners are 3 mm in length while the inner 12 electrodes are the pointy surface electrodes.

Muscle electrodes are typically designed to be the same length as hypodermic needles used for intramuscular injections, or 1.5 cm, see FIG. 1. The invasive skin electrodes can be a few millimeters in length, with 3 mm (see FIG. 2) having been used successfully in several pre-clinical animal research studies. The minimally invasive device uses pointy electrodes that may disrupt the stratum corneum to reach live tissue and achieve repeatable impedance measurements resulting in a robust and repeatable electroporation process. Combining the arrays can be achieved in many ways such as being different electrodes lengths in a grid, e.g., the 4×4, evenly distributed, square-like grid. The IM electrode can be the corners of 4×4 array, while the remaining 12 electrodes can be either 3 mm invasive dermal or the pointy surface dermal style, see FIG. 3. The corners could also be 3 mm in length while the inner 12 electrodes are the pointy surface electrodes, see FIG. 4. An alternate configuration could have the penetrating electrodes on a circle with the longer IM electrodes in different angular locations than the shorter invasive dermal electrodes. Alternatively, the configuration of the arrays can be other geometric like shapes, e.g., circular, triangular, rhomboid, parallelogram, etc, but keeping electrodes evenly distributed within each geometric configuration. In some embodiments, the lengths of the electrodes for IM penetration can be manipulated so as to penetrate shallower or deeper into the muscle; while the lengths for the ID penetration can vary from lengths that do not penetrate skin, to just penetrating through the stratum corneum, to that penetrating the subcutaneous layer, to that penetrating deep into the dermis.

In any of the cases, the each set of electrodes (ID or IM) are most likely to fired (electrical pulses) independently of the second set, with the order not expected to be significant. The electrodes could be fired in a multitude of patterns for a given treatment to achieve optimized performance of each method for a given therapy.

Figure 5:
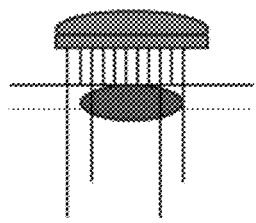
FIG. 5 shows the ID injection being passed by the invasive IM electrode portion of one of the embodiment of the invention.
Figure 6:
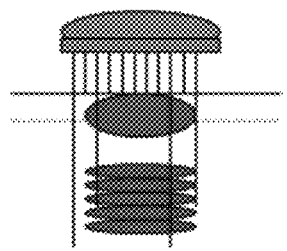
FIG. 6 shows the addition of the IM injection (in addition to that shown in FIG. 7) and demonstrates the additional transfection by the longer invasive electrodes, which locally treat the IM injection.
Figure 7:
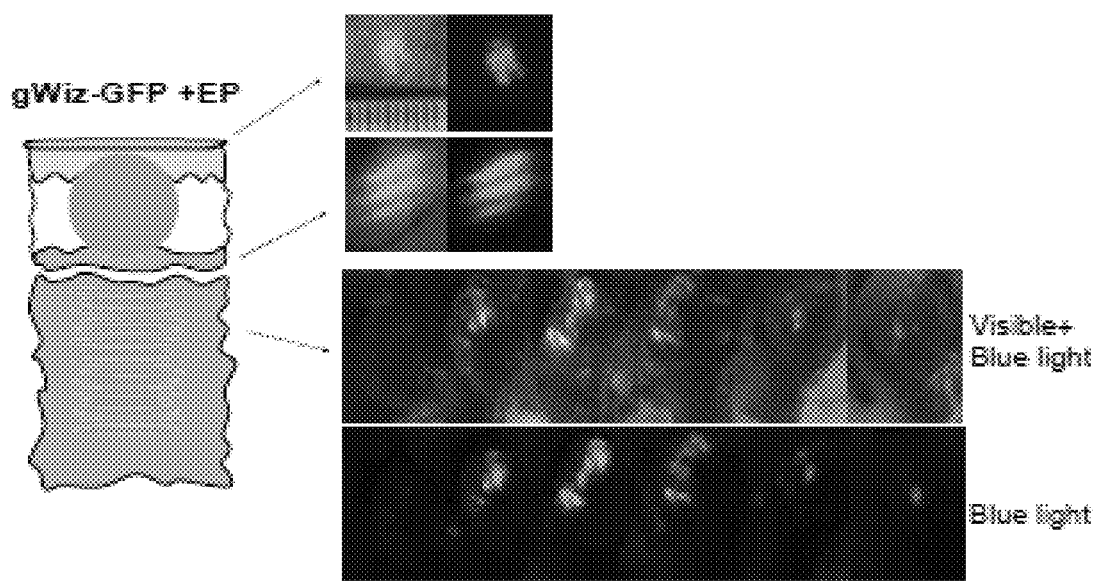
FIG. 7 shows the EP-enhanced GFP expression in the skin and underneath quadriceps muscle in a guinea pig model. The experimental skin and underneath muscle slices were analyzed by Olympus fluorescence microscope (objective 0.14×). In the control group without EP, the skin and muscle injected with DNA alone, the GFP expression was undetectable.
Figure 8:
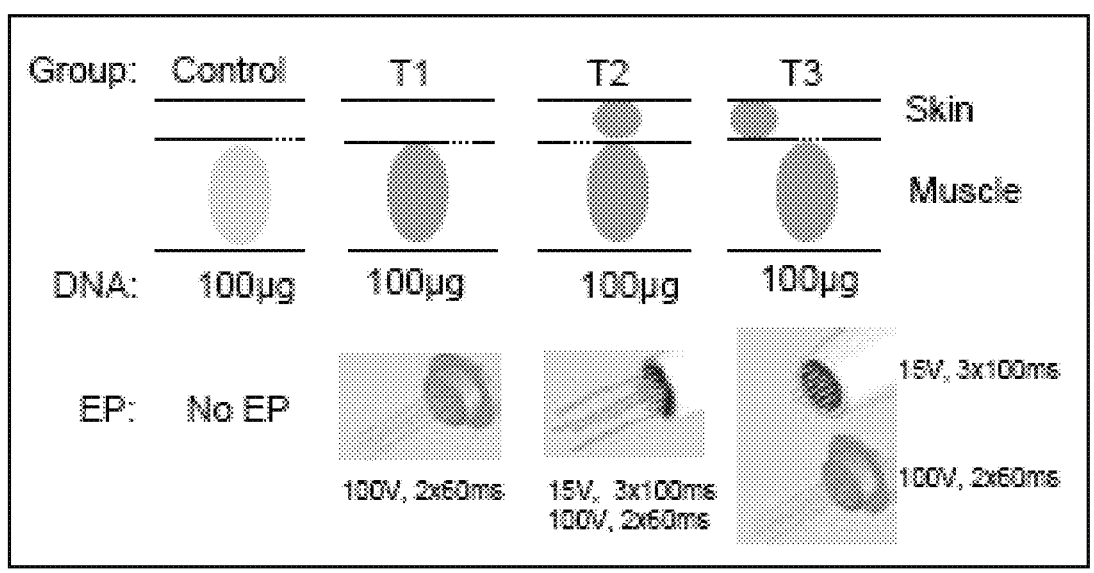
FIG. 8 displays a drawing showing the dual depth electroporation delivery in comparison to ID or IM alone.
Figure 9:
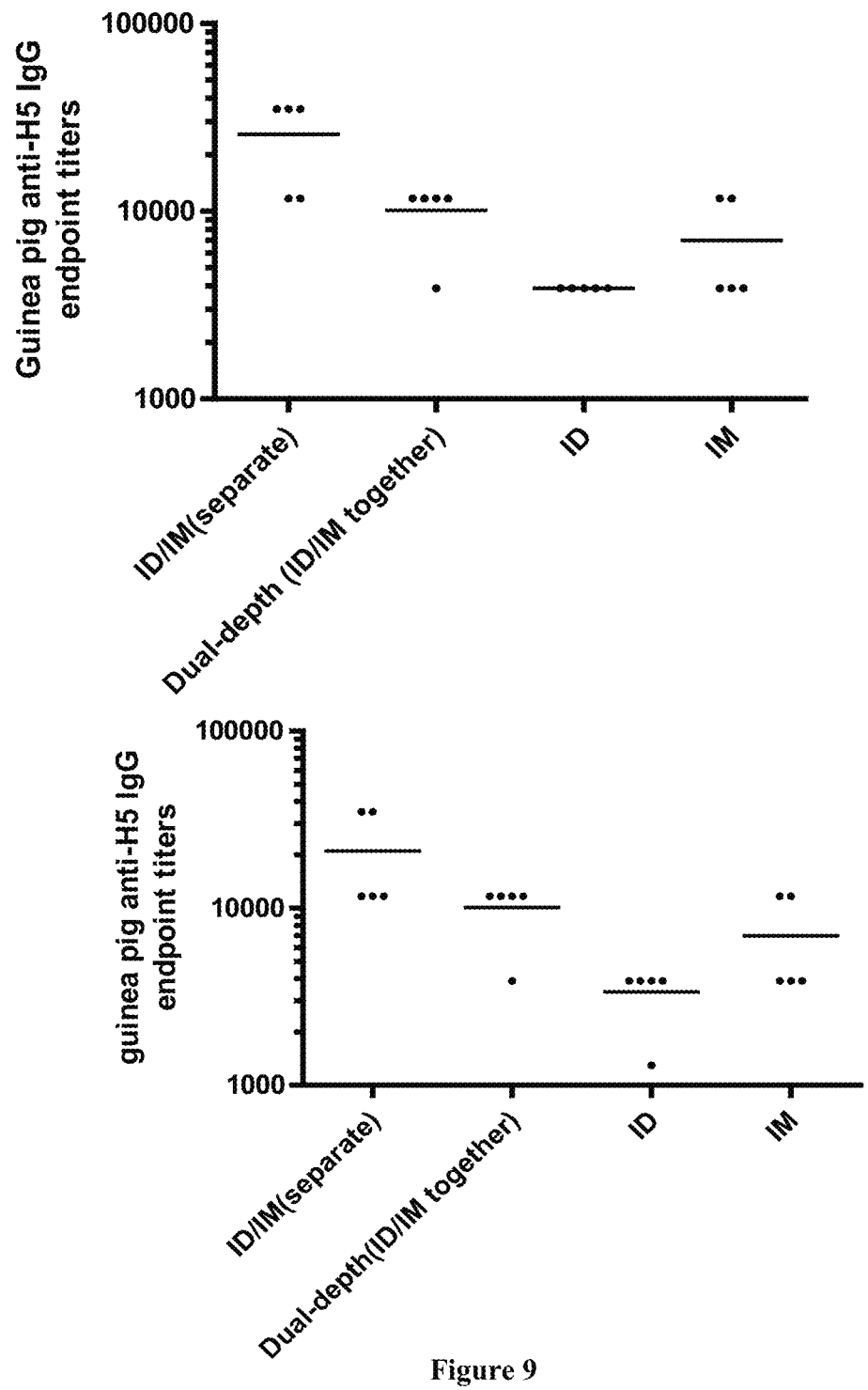
FIG. 9 displays graphs that depict antibody responses from vaccinated guinea pigs using one of the preferred embodiments.
Figure 10:
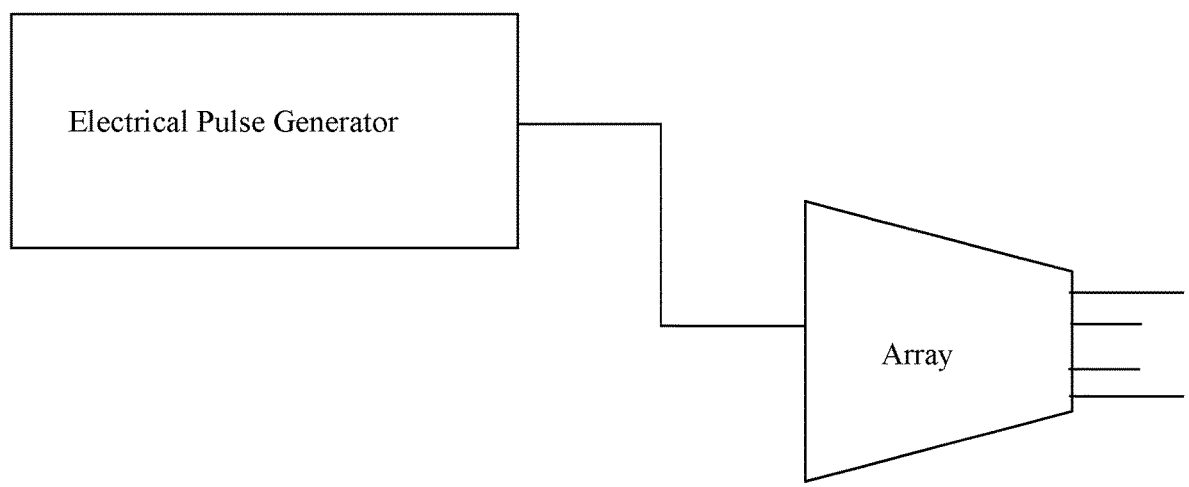
FIG. 10 displays an array with a first set of electrodes and a second set of electrodes in electrical communication with an electrical pulse generator.

FIG. 5 shows the ID injection being passed by the invasive IM electrode portion of the array and locally treated by the minimally invasive pointy electrodes. FIG. 6 shows the addition of the IM injection and demonstrates that only the longer invasive electrodes locally treat the IM injection.

Further aspects of the present invention include an electroporation device combining two sets of the provided dual depth electrodes for two or more different spatially separated tissue targets. One set of electrodes approximately 10-25 mm in length, is set for IM treatments. The second set of electrodes approximately 1-4 mm in length is set for invasive ID. The second set of electrodes can have a sharp distal end (or be pointy), intending only to disrupt the Stratum corneum (15-30 cell layers thick), i.e., sharp but not deeply penetrating for minimally invasive ID.

One set of electrodes can be assembled so as to float mechanically from the other set of electrodes, in order to allow the natural "seating" and conformance necessary to achieve proper contact.

In some embodiments, the electrodes are individually addressable for delivery of electrical pulses to allow for a multitude of firing patterns, sequences or combined in a multitude of patterns and sequences and fired in these groupings.

The electroporation device pulse parameters can be an optimized set for each individual treatment in the following ranges:

Intramuscular electroporation: voltage ranges can be selected from between 1V to 200V, 10V to 200V, 20V to 200V, 40V to 200V, 60V to 200V, 80V to 200V, 100V to 200V, 10V to 180V, 20V to 180V, 40V to 180V, 60V to 180V, 80V to 180V, 100V to 180V, 10V to 160V, 20V to 160V, 40V to 160V, 60V to 160V, 80V to 160V, 100V to 160V, 10V to 140V, 20V to 140V, 40V to 140V, 60V to 140V, 80V to 140V, 100V to 140V, 10V to 120V, 20V to 120V, 40V to 120V, 60V to 120V, 80V to 120V, or 100V to 120V, and preferably 100 V; current ranges can be selected from between 5 mA to 1 A, 100 mA to 1 A, 200 mA to 1 A, 300 mA to 1 A, 400 mA to 1 A, 500 mA to 1 A, 600 mA to 1 A, 700 mA to 1 A, 800 mA to 1 A, 900 mA to 1 A, 100 mA to 900 mA, 200 mA to 900 mA, 300 mA to 900 mA, 400 mA to 900 mA, 500 mA to 900 mA, 600 mA to 900 mA, 700 mA to 900 mA, 800 mA to 900 mA, 100 mA to 800 mA, 200 mA to 800 mA, 300 mA to 800 mA, 400 mA to 800 mA, 500 mA to 800 mA, 600 mA to 800 mA, 700 mA to 800 mA, 100 mA to 700 mA, 200 mA to 700 mA, 300 mA to 700 mA, 400 mA to 700 mA, 500 mA to 700 mA, 600 mA to 700 mA, 100 mA to 600 mA, 200 mA to 600 mA, 300 mA to 600 mA, 400 mA to 600 mA, 500 mA to 600 mA, 100 mA to 500 mA, 200 mA to 500 mA, 300 mA to 500 mA, or 400 mA to 500 mA; and 1, 2, 3, 4, 5, or 6 pulses; and pulse durations of between 5 ms and 250 ms, 20 ms and 250 ms, 40 ms and 250 ms, 60 ms and 250 ms, 80 ms and 250 ms, 100 ms and 250 ms, 20 ms and 200 ms, 40 ms and 200 ms, 60 ms and 200 ms, 80 ms and 200 ms, 100 ms and 200 ms, 20 ms and 150 ms, 40 ms and 150 ms, 60 ms and 150 ms, 80 ms and 150 ms, 100 ms and 150 ms, 20 ms and 100 ms, 40 ms and 100 ms, 60 ms and 100 ms, 80 ms and 100 ms, and preferably 100 ms.

ID invasive: voltage ranges can be selected from between 1V to 200V, 10V to 200V, 20V to 200V, 40V to 200V, 60V to 200V, 80V to 200V, 100V to 200V, 10V to 180V, 20V to 180V, 40V to 180V, 60V to 180V, 80V to 180V, 100V to 180V, 10V to 160V, 20V to 160V, 40V to 160V, 60V to 160V, 80V to 160V, 100V to 160V, 10V to 140V, 20V to 140V, 40V to 140V, 60V to 140V, 80V to 140V, 100V to 140V, 10V to 120V, 20V to 120V, 40V to 120V, 60V to 120V, 80V to 120V, or 100V to 120V, and preferably 100 V; current ranges can be selected from between 5 mA to 1 A, 100 mA to 1 A, 200 mA to 1 A, 300 mA to 1 A, 400 mA to 1 A, 500 mA to 1 A, 600 mA to 1 A, 700 mA to 1 A, 800 mA to 1 A, 900 mA to 1 A, 100 mA to 900 mA, 200 mA to 900 mA, 300 mA to 900 mA, 400 mA to 900 mA, 500 mA to 900 mA, 600 mA to 900 mA, 700 mA to 900 mA, 800 mA to 900 mA, 100 mA to 800 mA, 200 mA to 800 mA, 300 mA to 800 mA, 400 mA to 800 mA, 500 mA to 800 mA, 600 mA to 800 mA, 700 mA to 800 mA, 100 mA to 700 mA, 200 mA to 700 mA, 300 mA to 700 mA, 400 mA to 700 mA, 500 mA to 700 mA, 600 mA to 700 mA, 100 mA to 600 mA, 200 mA to 600 mA, 300 mA to 600 mA, 400 mA to 600 mA, 500 mA to 600 mA, 100 mA to 500 mA, 200 mA to 500 mA, 300 mA to 500 mA, or 400 mA to 500 mA; and 1, 2, 3, 4, 5, or 6 pulses; and pulse durations of between 5 ms and 250 ms, 20 ms and 250 ms, 40 ms and 250 ms, 60 ms and 250 ms, 80 ms and 250 ms, 100 ms and 250 ms, 20 ms and 200 ms, 40 ms and 200 ms, 60 ms and 200 ms, 80 ms and 200 ms, 100 ms and 200 ms, 20 ms and 150 ms, 40 ms and 150 ms, 60 ms and 150 ms, 80 ms and 150 ms, 100 ms and 150 ms, 20 ms and 100 ms, 40 ms and 100 ms, 60 ms and 100 ms, 80 ms and 100 ms, and preferably 100 ms.

ID minimally invasive: voltage ranges can be selected from between 1V to 70V, 1V to 50V, 5V to 50V, 10V to 50V, 12V to 50V, 15V to 50V, 1V to 40V, 5V to 40V, 10V to 40V, 12V to 40V, 15V to 40V, 5V to 30V, 10V to 30V, 12V to 30V, 15V to 30V, 5V to 20V, 10V to 20V, 12V to 20V, or 15V to 20V, and preferably 15V, current ranges can be selected from between 1 mA to 100 mA, 10 mA to 100 mA, 20 mA to 100 mA, 30 mA to 100 mA, 40 mA to 100 mA, 50 mA to 100 mA, 60 mA to 100 mA, 70 mA to 100 mA, 80 mA to 100 mA, or 90 mA to 100 mA; and 1, 2, 3, 4, 5, or 6 pulses; and pulse durations of between 5 ms and 250 ms, 20 ms and 250 ms, 40 ms and 250 ms, 60 ms and 250 ms, 80 ms and 250 ms, 100 ms and 250 ms, 20 ms and 200 ms, 40 ms and 200 ms, 60 ms and 200 ms, 80 ms and 200 ms, 100 ms and 200 ms, 20 ms and 150 ms, 40 ms and 150 ms, 60 ms and 150 ms, 80 ms and 150 ms, 100 ms and 150 ms, 20 ms and 100 ms, 40 ms and 100 ms, 60 ms and 100 ms, 80 ms and 100 ms, and preferably 100 ms.

The electroporation device preferably delivers (injects) a drug through a mechanized or automated manner. Preferably, this automated delivery component is an integral part of the device and activate or initiated to deliver the drug prior to EP treatment.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Animals: Hartley guinea pigs, female, 4 weeks of age with weights between 300 and 350 g, were used in the study (n=5). Animals were housed at Bio-quant, Inc., San Diego, Calif., in accordance with the standards of IACUC.

Plasmids: gWiz-GFP (Aldevron LLC, ND) and pGX2001 were used in the study. pGX2001encodes a consensus sequence of H5HA.

Immunization: H5HA vaccine was delivered ID and/or IM in guinea pigs with and without EP, using skin or muscle or dual-depth EP device. A boost was performed 3 weeks after first immunization.

GFP Expression and Imaging. For GFP expression analysis, gWiz GFP (0.5 mg/ml) was injected ID and IM in the skin (50 μl) and underneath quadriceps muscle (150 μl) followed by EP, guinea pigs were sacrificed at day 3, and the skin and muscle samples were taken and frozen at −20° C. Muscle samples were sectioned at 1.5 mm thickness, consecutive slices were lined up for image analyses using OV-100 fluorescence microscope.

ELISA. Blood samples were collected via jugular vein at weeks 2, 3 and 5 after the first immunization with a boost at week 3 and analyzed for anti-H5 antibody endpoint titers using ELISA. Ninety-six well plates were coated with 15 ng/well of recombinant H5HA (Immune Tech Corp, NY) to determine H5HA responses.

Guinea Pig Titers—Enhanced anti-H5HA antibody end-point titers using Dual-depth delivery.

Guinea pigs were primed with pGX2001 and boosted once at week 3. Samples were collected at days 14, 21, and 35, and analyzed by ELISA. The time course of anti-H3HA antibody titers are shown as mean±S.D. (n=5). All groups wherewith DNA injection followed by electroporation showed significantly higher antibody titers than that of DNA injection alone (* indicates $p<0.05$). See FIG. 9.

What is claimed is:

1. A dual depth electroporation device capable of electroporating both muscle tissue and skin tissue in a single application, comprising:

an electrical pulse generator;

an array in electrical communication with said electrical pulse generator, said array having a first set of electrodes and a second set of electrodes;

wherein the first set of electrodes is for intramuscular delivery of a first electric pulse, the first set of electrodes having a length of about 10 mm to about 35 mm, and wherein the second set of electrodes is for intradermal delivery of a second electric pulse, the second set of electrodes having a length of about 0.01 mm to about 4 mm, and wherein the array is configured such that the first set of electrodes is positioned for intramuscular delivery at the same time the second set of electrodes is positioned for intradermal delivery.

2. The device of claim 1, wherein the first electric pulse is delivered to muscle tissue and the second electric pulse is delivered to skin tissue.

3. The device of claim 2, wherein the electrical pulse generator delivers through the first set of electrodes the first electric pulse of from 1 volt to about 200 volts and the electrical pulse generator delivers through the second set of electrodes the second electric pulse of from 1 volt to about 200 volts.

4. The device of claim 3, wherein the electrical pulse generator delivers through the second set of electrodes the second electric pulse of from 1 volt to about 50 volts.

5. The device of claim 2, wherein the electrical pulse generator delivers through the first set of electrodes the first electric pulse of about 100 volts and the electrical pulse generator delivers through the second set of electrodes the second electric pulse of about 15 volts.

6. The device of claim 2, wherein each first electric pulse and the second electric pulse, individually, is repeated up to 6 times.

7. The device of claim 2, wherein the first electric pulse is repeated two times, and the second electric pulse is repeated three times.

8. The device of claim 2, wherein sequentially the first electric pulse occurs first and the second electric pulse occurs second.

9. The device of claim 2, wherein the first electric pulse delivers a current of from about 50 mA to about 500 mA, and the second electric pulse delivers a current of from about 50 mA to about 500 mA or from about 1 mA to about 50 mA.

10. The device of claim 2, wherein the first electric pulse delivers a current of about 400 mA, and the second electric pulse delivers a current of about 100 mA or about 10 mA.

11. The device of claim 2, wherein each of the first electric pulse and second electric pulse, individually, has a duration from 5 msec to about 250 msec.

12. The device of claim 2, wherein the second set of electrodes have a sharp distal tip that allows penetration of the skin tissue through the stratum corneum into the underlying epidermal tissue above the basal layer.

13. A method of generating a broad immune response in a subject by administering a biomolecule to both muscle tissue and skin tissue by electroporation assisted delivery using a dual depth electroporation device according to claim 1, comprising:

injecting a biomolecule to both muscle and skin tissue;

inserting the array, comprising inserting the first set of electrodes into muscle tissue and inserting the second set of electrodes into skin tissue;

delivering through the first set of electrodes the first electric pulse to the muscle tissue and through the second set of electrodes the second electric pulse to the skin tissue to permit transfection of the biomolecule; and allowing subject's immune system to generate broad immune response including humoral and cellular response to the injected biomolecule.

14. The method of claim 13, wherein the injecting step occurs prior to the inserting step.

15. The method of claim 13, wherein the delivering step comprises delivering through the first set of electrodes the first electric pulse of from 1 volt to about 200 volts and delivering through the second set of electrodes the second electric pulse of from 1 volt to about 200 volts.

16. The method of claim 15, wherein the delivering step comprises delivering through the second set of electrodes the second electric pulse of from 1 volt to about 50 volts.

17. The method of claim 13, wherein the delivering step comprises repeating each of the delivering of the first electric pulse and the delivering of the second electric pulse, individually, up to 6 times.

18. The method of claim 13, wherein the delivering step comprises, sequentially, the delivering of the first electric pulse first and the delivering of the second electric pulse second.

19. The method of claim 13, wherein the delivering step comprises the first electric pulse delivering a current of from about 50 mA to about 500 mA, and the second electric pulse delivering a current of from about 50 mA to about 500 mA or from about 1 mA to about 50 mA.

20. The method of claim 13, wherein the delivering step comprises the first electric pulse delivering a current of about 400 mA, and the second electric pulse delivering a current of about 100 mA or about 10 mA.

21. The method of claim 13, wherein the delivering step comprises delivering the first electric pulse for a duration from 5 msec to about 250 msec and delivering the second electric pulse for a duration from 5 msec to about 250 msec.

* * * * *